United States Patent [19]

Rothenberg

[11] Patent Number: 5,674,681
[45] Date of Patent: Oct. 7, 1997

[54] METHODS TO IDENTIFY HEMOCHROMATOSIS

[76] Inventor: Barry E. Rothenberg, P.O. Box 997, Del Mar, Calif. 92014

[21] Appl. No.: 349,883

[22] Filed: Dec. 6, 1994

[51] Int. Cl.$^6$ .......................... C12Q 1/68; C12P 19/34; G01N 33/53
[52] U.S. Cl. .......................... 435/6; 435/91.1; 435/91.2; 435/7.1
[58] Field of Search .......................... 435/6, 91.2, 91.1, 435/7.1

[56] References Cited

U.S. PATENT DOCUMENTS 4,970,296  11/1990  Saito et al. .......................... 530/323

OTHER PUBLICATIONS

Rothenberg et al., *Proc. Natl. Acad Sci. USA* 93, 1529–1534 (1996).
Simon et al., *Am. J. Hum. Genet.* 41, 89–105 (1987).
Jazwinska et al., *Am. J. Hum. Genet.* 53, 347–352 (1993).
Worwood et al., *Brit. J. Haematol.* 86, 863–866 (1994 Apr.).
Simon et al., *Ann. N.Y. Acad. Sci.* 526, 11–22 (1988).
Rothenberg et al., *FASEB J.* 8(5), A900 (1994 Mar.).
Svejgaard et al., *Lancet* 2, 547–549 (1976).
De Sousa et al., *Immunol. Lett.* 39(2), 105–111 (1994).
Rothenberg, Barry "The self recognition concept: An active function for the molecules of the major histocompatibility complex based on the complementary interaction of protein and carbohydrate." *Dev. and Comparative Immunol.* 2:23–38 (1978).
Shur, Barry D., "Glycosyltransferases as cell adhesion molecules." *Curr. Opinion Cell Biol.* 5:854–863 (1993).
Hinek et al., "The 67–kD Elastin/Laminin–binding protein is related to an enzymatically inactive, alternatively spliced form of β–Galactosidase." *J. Clin. Invest.* 91:1198–1205 (1993).
Miller et al., "Complementarity between sperm surface β–1,4–galactosyltransferase and egg–coat ZP3 mediates sperm–egg binding." *Nature* 357:589–593 (1992).

Scott et al., "A family of concanavalin A–binding peptides from a hexapeptide epitope library." *Proc. Natl. Acad. Sci. (USA).* 89:5398–5402 (1992).
Oldenburg et al., "Peptide ligands for a sugar–binding protein isolated from a random peptide library." *Proc. Natl. Acad. Sci. USA.* 89:5393–5397 (1992).
Sjoberg et al., "Natural ligands of the B cell adhesion molecule CD22β can be masked by 9–O–acetylation of sialic acids." *J. Cell Biol.* 126:549–562 (1994).
Powell et al., "Natural ligands of the B cell adhesion molecule CD22β carry N–linked oligosaccharides with α–2, 6–linked sialic acids that are required for recognition." *J. Biol. Chem.* 268(10):7019–7027 (1993).
Powell and Varki, "The oligosaccharide binding specificities of CD22β, a sialic acid–specific lectin of B cells." *J. Biol. Chem.* 269(14):10628–10636 (1994).
Iwata et al., "Membrane receptors of mouse lymphocytes for various lectins." *J. of Biochem.* 82(3):661–669 (1977).
Nag et al., "N–linked oligosaccharides of murine major histocompatibility complex class II molecule." *J. of Biol. Chem.* 267(31):22624–22629 (1992).
Bezouska et al., "Characterization of the high–affinity oligosaccharide–binding site of the 205–kDa porcine large granular lymphocyte lectin, a member of the leukocyte common antigen family." *European J. of Biochem.*, 213:1303–1313 (1993).
Thor et al., "Monoclonal antibody that distinguishes between a phosphorylated, β$_2$–Microglobulin–Associated, and a free, nonphosphorylated, chain of MHC class I." *J. Immunol.*, 151(1):211–224 (1993).
Rothenberg et al., "Biotinylated diaminopyridine: An approach to tagging oliogsaccharides and exploring their biology." *Proceedings of the National Academy of Sciences USA*, 90:11939–11943 (1993).
Stamenkovic et al., "The B lymphocyte adhesion molecule CD22 interacts with leukocyte common antigen CD45RO on T cells and α2–6 sialytransferase, CD75, on B cells." *Cell*, 66:1133–1144 (1991).

*Primary Examiner*—Kenneth R. Horlick
*Attorney, Agent, or Firm*—Fish & Richardson P.C.

[57] ABSTRACT

The present invention provides methods to identify hemochromatosis in an individual. For example, the invention provides a method of detecting reduced association of $\beta_2$-microglobulin with a nonclassical MHC class I heavy chain molecule or a mutation in nonclassical MHC class I heavy chain-encoding DNA which results in a reduction of $\beta_2$-microglobulin-heavy chain association indicating that the individual tested has or is at risk of having hemochromatosis.

11 Claims, No Drawings

METHODS TO IDENTIFY HEMOCHROMATOSIS

BACKGROUND OF THE INVENTION

1. Field of the Invention

This invention relates generally to the field of immunological disorders and, more specifically, to major histocompatibility complex transplantation molecules.

2. Background Information

The major histocompatibility complex (MHC) codes for a variety of gene products, many of which play a central role in the body's defense against pathogenic organisms. Such molecules include the classical transplantation antigens and structurally related molecules, proteins for transport of foreign peptides within cells, serum complement proteins, the lymphokines tumor necrosis α and tumor necrosis β, cytochromes and heat shock proteins.

The classical transplantation antigens, encoded for by genes in the MHC, are a highly polymorphic group of molecules that were originally discovered for their role in determining rejection of foreign transplanted cells and tissue. An extensive body of experimental work has since supported a role for the classical transplantation antigens in self-recognition. In the current paradigm, transplantation antigens serve to present peptides derived from both self and foreign proteins, for recognition by cells of the immune system.

Two distinct groups of antigens, class I and class II antigens, are encoded by genes within the MHC. Class I antigens are expressed on virtually all nucleated cells in the body and play a role in the mediation of immune responses based on cytotoxic thymus-derived (T) lymphocyte mediated cell killing. Cytotoxic T lymphocytes play a role in killing of virus infected cells and tumor cells. The class I MHC molecule is composed of a 45 kiloDalton (kDa) heavy chain associated non-covalently with a 12 kDa protein known as $\beta_2$ microglobulin ($\beta_2$M). The present paradigm characterizes class I antigens as presenting peptide fragments derived from both self and foreign proteins synthesized endogenously within the cell.

The class I molecules were discovered for their role in transplantation and were termed the "classical" class I molecules, to distinguish them from a later discovered group of class I molecules termed the "nonclassical" class I molecules. Genes encoding the nonclassical class I MHC molecules consist of the majority of genes so far identified in the MHC locus. Nonclassical class I MHC molecules are overall structurally related to the classical class I MHC transplantation antigens in having extensive sequence homology and a heavy chain noncovalently associated with $\beta_2$M. Nonclassical class I MHC molecules are, in general, less polymorphic than the classical class I MHC molecules and are more circumscribed in their tissue distribution. Several types of nonclassical class I molecules are expressed principally in the gastrointestinal (GI) tract, raising questions regarding their function, if any in the immune system.

MHC class II antigens are expressed principally by specialized antigen presenting cells in the body. Such cells are limited to the antibody producing B lymphocyte as well as macrophages and dendritic cells distributed in various tissues of the body. The class II molecule on the cell-surface is composed of an α chain of 33 kDa and a β chain of 28 kDa associated noncovalently. Class II molecules as presently understood function principally to present peptides derived from self or foreign proteins to a specialized class of T lymphocyte that supports the development of cytotoxic T lymphocytes, provides immunity to fungal infections and assists B lymphocytes in the generation of protective antibody responses to encapsulated bacterial infections. MHC class II antigens present peptide fragments derived from proteins taken up by cells from the surrounding environment, in contrast to classical class I molecules, which present peptides derived from endogenously synthesized proteins.

A variety of human autoimmune diseases have been shown to be associated more frequently in the population with individuals who inherit certain genes of the MHC. For many of these diseases, the association is localized to the region of the MHC encoding class II histocompatibility antigens. These diseases are not inherited by simple mendelian segregation of MHC genes, since only one sibling of a set of identical twins may have the disease. This feature suggests that other genetic factors or environmental factors have roles in the development of autoimmunity, with genes in the MHC playing a significant part of the process.

The current paradigm for MHC gene function provides several theories to explain a role for MHC genes in autoimmune disease. They include the inappropriate expression of class II MHC molecules in cells eliciting the autoimmune response or aberrant recognition of self-peptides by particular MHC gene products. Such theories, however, remain to be proven. In addition, the current paradigm fails to provide a useful hypothesis to explain the basis for an MHC-associated iron storage disease known as hemochromatosis. This disease is known from animal studies and from the genomic structure of several class I genes to involve an MHC encoded class I molecule since deletion of the $\beta_2$M gene in these animals results in the disease.

Thus, there exists a need to develop new approaches to the treatment of MHC associated diseases. The present invention is based on a new paradigm for the role of class I and class II antigens and other broadly related molecules in self-recognition and in regulation of the immune system. This paradigm provides that self-recognition molecules have a central function to recognize and modify carbohydrate structures. Thus, the present invention provides new methods for identifying carbohydrate ligands for self-recognition molecules and utilizing such ligands to treat diseases involving aberrant self-recognition such as autoimmune diseases, inflammatory diseases or susceptibility to infections and provides related advantages as well.

SUMMARY OF THE INVENTION

The present invention provides a substantially purified carbohydrate ligand that specifically binds to a leczyme. In addition, the invention provides methods to identify a carbohydrate ligand that specifically binds to a leczyme or a leczyme that specifically binds to a carbohydrate ligand. The invention further provides methods to identify a peptide that binds to the carbohydrate ligand binding-site of a leczyme.

The present invention also provides methods for isolating a carbohydrate ligand that binds to a leczyme or for isolating a leczyme that binds to a carbohydrate ligand. The invention further provides methods to identify a carbohydrate ligand or a leczyme that can modify the function of a cell and to obtain such functionally modified cells.

The invention also provides methods for modifying a cell to produce a carbohydrate ligand by introducing an expression vector encoding a leczyme into the cell, wherein the expression of the leczyme produces the carbohydrate ligand.

The invention also provides methods for modulating an immune response to an antigen by administering the antigen and a carbohydrate ligand.

The invention also provides methods for treating a disease state involving a leczyme by administering an effective amount of a carbohydrate ligand that binds to the leczyme involved in the disease state or by administering an effective amount of a leczyme that has a similar binding specificity to the leczyme involved in the disease state.

The invention further provides methods to diagnose a genetic basis for hemochromatosis by detecting a mutation in a class I MHC molecule that reduces it's ability to associate with $\beta_2$ microglobulin.

DETAILED DESCRIPTION OF THE INVENTION

The present invention results from a profound new paradigm for the function of self-recognition molecules in organisms including mammals. The new paradigm holds that many types of self-recognition molecules heretofore known as peptide recognition and presentation structures have a more central function in the recognition and modification of carbohydrate-based molecules. Although the current paradigm does not exclude recognition of peptide that is bound to a carbohydrate, such as a peptide derived from a glycoprotein, the current paradigm provides that it is the peptide rather than the carbohydrate that is bound by the self-recognition receptor molecule. Thus, self-recognition molecules of the new paradigm have the ability to specifically bind a substrate carbohydrate structure and chemically modify it either by catalyzing further addition of carbohydrate or by catalyzing chemical modification of the existing carbohydrate. Additionally, after enzymatic modification, the self-recognition molecule can specifically bind with equivalent or greater affinity to the modified carbohydrate structure than to the substrate originally recognized.

A molecule whose function includes the enzymatic modification of carbohydrate and the recognition of the enzymatic product has been termed a "leczyme" based on the combination of having both lectin-binding and enzymatic activity in the same base molecule. The present invention provides that leczyme function is characteristic of many peptide recognition molecules that are well known in the art. Such molecules include the class I and class II MHC encoded molecules and other members of the immunoglobulin gene superfamily (IgGSF) of molecules. In addition, leczyme function also can be associated with nonclassical class I molecules.

As used herein, "leczyme" defines a cellular protein, which can catalyze the chemical modification of a substrate resulting in a product with additional carbohydrate or chemically modified carbohydrate. Leczymes also can catalyze chemical modifications of a carbohydrate molecule such as phosphorylation, acetylation, carboxylation or sulfation. A leczyme can enzymatically modify other leczymes or can modify non-leczyme molecules. In addition, a leczyme can be expressed in the cytoplasm, on the cell-surface or can be secreted from a cell and recognize its enzymatically modified product either expressed on a cell-surface or secreted from a cell.

A leczyme can exhibit enzymatic activity and carbohydrate binding activity in the same isoform of the molecule or these activities can reside separately in different isoforms of the molecule. For example, differential RNA splicing of a leczyme can result in an enzymatically active isoform of the leczyme which contains a signal(s) directing the leczyme to sites in the cell normally associated with glycosylation, such as the endoplasmic reticulum or the golgi complex. Differential RNA splicing can also result in an isoform of the leczyme that exhibits carbohydrate recognition capability and contains a signal(s) directing the receptor to the cell-surface or to export from the cell. Alternatively, a leczyme expressed either in the cell or on the cell-surface can contain both enzymatic activity as well as carbohydrate recognition capability in the same molecule.

Leczyme function can be resident in the groove formed at the top of MHC encoded classical class I or class II molecule, which is characterized in the current paradigm as a peptide-binding groove. The new paradigm provides that the groove functions principally to recognize a carbohydrate structure. In addition, a leczyme such as a classical class I or class II molecule is also endowed with the ability to catalyze the chemical modification of the carbohydrate structure it recognizes and to recognize the modified product.

The present invention provides compositions of substantially purified carbohydrate ligands that can bind to a leczyme. As used herein, the term "carbohydrate ligand" or "ligand" means a sugar-based molecule where the sugar is a part of the ligand that is recognized by the leczyme. A carbohydrate ligand can comprise one or more sugar residues. Multiple sugar residues of a carbohydrate ligand can be linked in either a straight chain or branched chain configuration.

Carbohydrate ligands composed of multiple sugar residues can vary in the type and location of the linkage between each residue. Sugar residues useful for producing a carbohydrate ligand include, for example, glucose, galactose, fucose, mannose and sialic acid. Sugar residues of a ligand also can be acetylated, phosphorylated or sulfated by chemically processes well known in the art. A carbohydrate ligand also can be chemically bonded to other molecules such as a lipid, glycolipid, protein, glycoprotein, proteoglycan, glucosaminoglycan or an organic molecule. Such additional molecules can provide the carbohydrate ligand with features such as increased binding to the leczyme or increased stability in vivo.

A carbohydrate ligand can be multivalent in nature by having more than one carbohydrate ligand attached to a backbone structure. The backbone structure can be a natural protein such as a serum albumin or can be a synthetic molecule such as a synthetic peptide. Approaches to link multiple carbohydrate ligands to a backbone structure are known in the art and include, for example, biotin-avidin linkage (Rothenberg et al., *Proc. Natl. Acad. Sci. (USA)* 90:11939–11943 (1993), which is incorporated herein by reference).

The knowledge that a self-recognition molecule is a leczyme and that it has been selected through evolution to recognize and modify a carbohydrate structure such as a carbohydrate ligand provides new methods to treat disease states resulting from such self-recognition leczymes. Such disease states include, for example, autoimmunity, hemochromatosis, inflammation, transplantation rejection, and infections. In many of the above disease states, disease results from aberrant recognition of self-carbohydrate structures by lymphocytes. Thus, the administration of a carbohydrate ligand that can bind to the aberrant self-recognition molecule of an individual provides a means to disrupt the aberrant self-recognition cycle mediating the disease.

A variety of leczymes exist that differ in their ability to modify particular types of molecules. This difference results from differences in the specificity of the lectin binding site that leczymes have for their substrate. Thus, a part of the leczyme structure is a recognition site for the substrate. The catalytic site of a leczyme can be the same site as the substrate recognition site or can be a site different from the substrate recognition site. After modification of the substrate, the leczyme can exhibit similar or greater binding affinity for the modified substrate over the original substrate due to coordinate binding by both the substrate recognition site and the catalytic site of the leczyme or by multivalency of the ligand.

Leczymes utilized in the present invention include a broad group of structurally related molecules, many of which are contained within the IGSF. The IgGSF series of genes share an evolutionary homology (ie. common ancestor) but are not necessarily functionally related, genetically linked or coordinately regulated. The products of the IgGSF have been defined by the presence of one or more regions homologous to the basic structural unit of immunoglobulin (Ig), known as the Ig homology unit. These units are characterized by a primary amino acid sequence of about 70–100 residues in length and include an essentially invariant disulfide bridge spanning 50–70 residues in length and several other relatively conserved residues that maintain a tertiary structure known as the Ig fold (for review see Hunkapiller and Hood, *Adv. Immunol.,* 44:1–63, (1989)).

The genes of the IgGSF encode many molecules with known immunological function, such as the immunoglobulins, T lymphocyte receptors, classical and nonclassical MHC molecules, various T lymphocyte and B lymphocyte cell-surface molecules or $\beta_2 M$. In addition, the IgGSF encodes several cell-surface molecules known to function as receptors for cell-cell adhesion. Such adhesion molecules include, for example, the neural cell adhesion molecule carcinoembryonic antigen. Those IgGSF molecules devoted exclusively to mediating cell adhesion or immunological recognition such as immunoglobulins or the T cell receptor are not a leczyme.

Leczymes of the IgGSF are encoded by genes located within the MHC region. In humans, the MHC is in a continuous stretch of DNA located on the short arm of chromosome 6. The entire MHC in humans is called the HLA complex. In mice, the MHC is located on chromosome 17 and contains the H-2, Q, T and M complexes. As used herein, the term "MHC-derived gene product" means any molecule that contains at least one polypeptide encoded for by a gene located within the MHC. Leczymes that are MHC-derived gene products include class I and class II molecules. Class I and class II molecules that are leczymes in humans are encoded by genes within the HLA-D region such as HLA-DP, HLA-DN, HLA-DM, HLA-DO, HLA-DQ or HLA-DR, or the various alleles of HLA-A, HLA-B and HLA-C loci, or the HLA-X, HLA-E, HLA-J, HLA-H, HLA-G and HLA-F genes.

Leczymes that are class I MHC molecules contain a 45 kDa polymorphic heavy chain or $\alpha$ chain associated noncovalently with a small nonpolymorphic protein called $\beta_2 M$. The heavy chain is an MHC-encoded gene product located in or near the A, B or C regions of the human HLA complex and within or near the K or D/L regions of the mouse H-2 complex. Although $\beta_2 M$ is encoded by a gene located outside the MHC and on a different chromosome, the heavy chain of the class I molecule is encoded by a gene located within the MHC, thereby including a class I molecule within the definition of an MHC-encoded gene product.

Leczymes that are class II MHC molecules are MHC-derived gene products composed of a 34 kDa $\alpha$ chain associated noncovalently with a 28 kDa $\beta$ chain. An additional chain called the invariant chain is transiently associated with the class II heterodimer during transport to the plasma membrane of the cell.

Leczymes can be expressed on the cell-surface by virtue of having a transmembrane region and cytoplasmic tail, as in the case of the classical transplantation antigens. Leczymes also can be linked to the cell-surface in a manner similar to some nonclassical class I molecules. For example, many of the nonclassical class I Qa and Tla molecules are linked to the cell-surface by a phosphatidylinositol (PI) linkages, and the product of the Q10 gene appears to be secreted (Devlin et al., *EMBO J.* 4:369–374 (1985)). The majority of Qa and Tla antigens lack the classical class I cytoplasmic exons including the phosphorylation site in exon seven (Thor et al., *J. Immunol.,* 151:211–224 (1993)), although the transmembrane domain and the seventh exon is present in Q1 and Q2 gene products.

The MHC class I heavy chain is organized into three external domains ($\alpha 1$, $\alpha 2$ and $\alpha 3$), each containing about 90 amino acids each, a transmembrane domain of about 40 amino acids and a cytoplasmic anchor segment of about 30 amino acids. $\beta_2 M$ is similar in size and in organization to the external $\alpha 3$ domain of the heavy chain. X-ray crystallographic analysis of the extracellular portion of the MHC class I molecule shows that the $\alpha 1$ and $\alpha 2$ domains interact and are most external to the cell membrane while the $\alpha 3$ and $\alpha_2 M$ domains interact and are more proximal to the cell membrane. The interacting $\alpha 1$ and $\alpha 2$ domains form a platform containing a deep groove or cleft located on the top surface of the molecule.

The current paradigm for the function of the classical class I MHC molecule interprets the groove at the top of the molecule as a peptide binding site. The site is sufficiently large enough to bind a peptide of about 8–20 residues in length and present both self and foreign-derived peptides for recognition by certain T lymphoid cells. Extensive research has shown that the MHC classical class I molecule can bind peptide of about the length of the groove. In addition, the x-ray crystallographic analysis of a classical class I molecule purified from a cell indicated that a peptide was resident in the groove. However, as described above, the new paradigm in the present invention provides that the peptide binding groove of the classical class I molecule MHC is suited for binding a carbohydrate ligand.

Leczymes that are a class II MHC molecule share significant structural features with a class I molecule. The class II molecule is a membrane bound glycoprotein that contains external domains, a transmembrane segment, and a cytoplasmic anchor segment. The $\alpha$ chain contains two external domains labelled $\alpha 1$ and $\alpha 2$ and the $\beta$ chain contains two external domains $\beta 1$ and $\beta 2$ domain. X-ray crystallography shows that the $\alpha 2$ and $\beta 2$ domains interact as a membrane proximal structure analogous to the $\alpha 3$ domain and $\beta_2 M$ domain interaction of the class I molecule. The $\alpha 2$ and $\beta 2$ domains of a class II molecule that together form a cleft at the top of the molecule that is very similar to the cleft formed by the a1 and a2 domains of a class I heavy chain. Extensive evidence indicates that the groove in the class II molecule can bind and present both self and foreign peptides for recognition by T lymphoid cells. Peptides have been isolated from the class II molecule that are from 13–18 amino acids in length, slightly longer that the octomeric or nonomeric peptides commonly isolated from MHC classical class I molecules. As discussed above, the new paradigm of the present invention provides that the peptide binding groove in the class II MHC molecule, like the groove in the classical class I MHC molecule is suited for binding a carbohydrate ligand.

Leczymes also are encoded by nonclassical class I genes. In the mouse, genes encoding leczymes are located in the MHC regions Q, T and M downstream of the classical histocompatibility antigens. There are similar regions in humans coding for known nonclassical class I molecules such as HLA-F and HLA-G. The nonclassical class I genes are overall less polymorphic than the classical class I genes and show different patterns of expression. The Q, T and M complex genes of mice consist of approximately 45 genes, coding for non-polymorphic differentiation antigens with limited tissue distribution.

Leczymes which are nonclassical class I MHC molecules exhibit limited tissue distribution in comparison with leczymes that are classical class I MHC molecules. For example, the Qa and Tla antigens, the products of the Q and T genes, are expressed on subpopulations of lymphocytes (for review, see Flaherty et al. *Critical Reviews in Immunology*, 10:131–175 (1990)). Previously, no convincing function had been assigned to the products of the nonclassical class I genes, although they have been suggested as possible restriction elements for γδ T cells (Hershberg et al. *Proc. Nat. Acad. Sci (USA)*, 87:9727–31 (1993)). The Qa and TLa antigens have also been reported to be expressed on intestinal epithelium (Wu et al, *J. Exp. Med.*, 174:213–218 (1991); Hershberg et al., *Proc. Natl. Acad. Sci. (USA)* 87:9727–97231 (1990); Wang et al., *Immunogenet.*, 38:370–372 (1993)) where their function was unknown. The new paradigm of the present invention provides that these nonclassical class I molecules are leczymes.

The nonclassical class I molecule Q2, produced by a gene within the mouse MHC, is an example of a leczyme that is involved in iron transport (see Example I). The gene for Q2 is located in a head to head relationship with another gene most likely encoding a mucin. Both genes share a single promoter region, located between the genes, the promoter being analogous in structure to the β-globin promoter involved in iron metabolism. The coordinated regulation of these two genes can be readily understood in view of the receptor/ligand and receptor/substrate interactions defined as leczyme function in the new paradigm. Interestingly, the Q2 gene is distinguished from other nonclassical class I genes in being highly polymorphic with Q2 molecules of different strains of mice differing significantly in amino acid sequence. Despite these differences, the Q2 molecules from separate strains of mice all function as a receptor for their co-regulated gene product since, as a leczyme, Q2 can enzymatically modify its ligand/substrate in accordance with the lectin recognition and enzymatic function of each Q2 gene product and can recognize the resulting product. Thus, the combined enzymatic/recognition capability of a leczyme as defined in the new paradigm maintains receptor/ligand relationships in the face of extensive genetic polymorphism.

Leczymes exist with a variety of enzymatic activities. For example, a leczyme can have as a glycosyl transferase enzymatic activity that results in the catalytic transfer of a glycosyl group (mono or oligosaccharide) from a glycosyl-nucleotide to an acceptor molecule such as a protein, carbohydrate or lipid. However, not all glycosyl transferases are leczymes. In fact, very few such enzymes would be leczymes since the overwhelming majority of glycosyltransferases are restricted to expression in the endoplasmic reticulum and golgi complex of the cell.

There is currently only one glycosyl transferase (β1,4-galactosyltransferase) that is previously known to be expressed in both the cytoplasm and on the cell (for a review see Shur, *Curr. Opin. in Cell Biol.*, 5:854–863 (1993)). This enzyme has both carbohydrate recognition capability and carbohydrate catalytic activity and has been implicated in a variety of cell-cell and cell-matrix interactions. One hallmark of the cell-surface expressed form of β1,4-galactosyltransferase is that it no longer retains binding activity for the product it generates after enzymatic modification (Miller et al., *Nature*, 357:590–593 (1992)). Thus, this particular transferase is not a leczyme because it fails to exhibit recognition for it's enzymatic product.

A Leczyme of the IgGSF can be encoded by a gene located outside the MHC. For example, CD-1 is a product of the IgGSF gene that is related in structure to the class I MHC molecule but the CD-1 heavy chain is encoded by a gene outside the MHC. The T-6 CD-1 molecule is expressed by a specialized antigen presenting cell in the skin (Langerhan's cell) and can be internalized along with MHC class II antigen, indicating an immunological function for T-6.

The present invention provides a composition, comprising a substantially purified carbohydrate ligand that is specifically bound by a leczyme. As used herein, the term "substantially purified" means a carbohydrate ligand that is relatively free from other contaminating molecules such as lipids, proteins, nucleic acids, carbohydrates or other molecules normally associated with a carbohydrate ligand in a cell or tissue. A substantially purified carbohydrate ligand can be obtained, for example, using well known biochemical methods of purification of a carbohydrate source or by chemical or enzymatic synthesis.

A carbohydrate ligand of the present invention can include known forms of carbohydrate containing molecules such as glycoproteins, proteoglycans, glycolipids or mucopolysaccharides that have N-linked or O-linked forms of glycosylation. The proteoglycans include, for example, mucins and those proteoglycans glycosylated with hyaluronate, chondroitin sulfate, heparin, heparan sulfate or dermatin sulfate. Glycolipids that contain carbohydrate ligands include, for example, acylglycerol, a sphingoid or a ceramide.

A sample containing a carbohydrate ligand can be obtained from a variety of sources such as from fluids, tissues or cells. These sources can be from any plant species or any animal such as a mammal or any organism. A source of carbohydrate ligand can also include a cell that has been modified by introducing into the cell an expression vector that encodes a leczyme or a protein that when expressed contains a carbohydrate ligand.

A sample containing a carbohydrate ligand can be obtained from a chemically produced library of carbohydrates. Such libraries can be made by mixing carbohydrates from natural sources and from enzymatically-produced sources. In addition, individual carbohydrates from the library can be tagged with a detectable label such as a fluorescent label to assist in structural determination of the carbohydrate ligand.

A sample containing a carbohydrate ligand can be processed to further purify the ligand by methods well known in the art. Such methods include, for example, purification of glycoconjugates, labelling of glycoconjugates by chemical or metabolic means, release of oligosaccharides from glycoconjugates and characterization of the structure of the released carbohydrate (see, for example, Ausubel et al, In *Current Protocols in Molecular Biology* Vol. 2, chapter 17, (Green Publishing Associates and Wiley Interscience, New York, 1994); Fukuda and Kobata, *Glycobiology: A practical Approach*, (IRL Press, New York, 1993), both of which are incorporated herein by reference). In addition, these methods are useful for structural characterization, including sequencing of the carbohydrate ligand. Elucidation of the structure of a carbohydrate ligand purified from a tissue or a cell can enable future production of the ligand by direct chemical synthesis or enzymatic synthesis or purification from a natural source.

The present invention provides methods to identify a carbohydrate ligand that can bind to a leczyme. In this method, a sample containing a carbohydrate ligand is contacted with a leczyme suspected of binding to the ligand under suitable conditions to allow specific binding of the ligand to the leczyme. Suitable conditions include, for example, an appropriate buffer concentration and pH and time and temperature that permits binding of the particular leczyme and the carbohydrate ligand. After a suitable reaction period, the amount of carbohydrate ligand bound to the leczyme can be determined, for example, by attaching a detectable moiety such as a radionuclide or a fluorescent label to the carbohydrate ligand and measuring the amount of label that is associated with the leczyme after any unbound carbohydrate ligand has been removed from the ligand-leczyme complex.

As used herein, "detectable label" means a molecule whose presence can be detected due to a physical, chemical or biological characteristic of the molecule. Detectable labels include, for example, radioisotopes, fluorescent molecules, enzyme/substrate systems, or visually detectable molecules. Methods for detectably labelling a carbohydrate molecule are well known in the art, and include, for example, reduction with $NaB(^3H)_4$ or synthesis with radiolabelled sugars (see, for example, Varki, surpa, 1994 and Rothenberg et al., *Proc. Natl. Acad. Sci. (USA)*, 90:11939–11943 (1993), both of which are incorporated herein by reference, and Fukuda and Kobata, supra 1993). In addition, kits for the preparation of a labelled carbohydrate molecule are readily available from commercial sources such as Oxford GlycoSystems (Rosedale, N.Y.).

Methods to remove unbound labelled ligand from the ligand-leczyme complex depend, for example, on attaching the leczyme to a solid support. Solid supports useful in the present invention and methods to attach proteins to such supports are well known in the art (see for example Harlow and Lane, *Antibodies: A laboratory Manual* (Cold Spring Harbor Laboratory Press, Cold Spring Harbor, N.Y., 1988), which is incorporated herein by reference). Such solid supports include, for example, Sepharose, agarose or polystyrene.

After a suitable reaction period and after any unbound label has been removed from the support by, for example, washing, the amount of label attached to the solid support provides a direct measurement of the amount of carbohydrate ligand bound to the leczyme on the support. Alternatively, the amount of labelled carbohydrate ligand bound to the support can be indirectly determined after the reaction period by measuring the amount of unbound label and subtracting this from the amount of label added at the start of the reaction.

To accurately determine the amount of labelled ligand that binds specifically to the leczyme, a control reaction can be performed where all conditions are the same as in the binding reaction between the labelled ligand and leczyme except that the leczyme is not included in the control reaction or the leczyme is replaced by an irrelevant protein such as a serum albumin. The control reaction determines the amount of binding of the labelled carbohydrate ligand that occurs nonspecifically such as the amount of labelled ligand that binds to the solid support rather than to the leczyme on the solid support. Thus, it is necessary to subtract the nonspecific binding value obtained from the control reaction from the binding value obtained from the reaction that included both the labelled carbohydrate ligand and the leczyme to determine the amount of ligand that specifically bound the leczyme under the conditions tested.

An advantage of using a solid support is that the labelled ligand can be added in excess relative to the leczyme, making it possible to identify lower levels of binding affinity between the carbohydrate ligand and the leczyme. Methods such as Scatchard analysis are well known in the art for determining the binding affinity between two molecules, both of which can be in solution or one of which can be attached to a solid support. Equilibrium dialysis is an example of a method where the binding of a ligand to leczyme can be determined when both molecules are in solution.

Methods to measure the binding of a labelled carbohydrate ligand to a leczyme also can be performed when the leczyme is associated with a cell. In a manner analogous to the use of solid supports, cells that express the leczyme on the cell-surface can bind the labelled carbohydrate ligand and, after a suitable reaction period, the cells can be separated from the unbound ligand by methods well known in the art such as by centrifugation or filtration. Cells that express a leczyme in the cytoplasm can also be used to detect binding of a carbohydrate ligand to the leczyme provided the cell membrane has been sufficiently permeabilized to allow access of the carbohydrate ligand to the leczyme in the cell. Methods that use cells in binding assays such as antigen-antibody binding assays are well known in the art (see, for example, Harlow and Lane supra, 1988) and are generally applicable to binding assays between a carbohydrate ligand and a leczyme.

A leczyme-expressing cell can be a cell that naturally expresses the leczyme such as a lymphocyte that expresses a class I or class II MHC encoded leczyme or can be a cell that expresses the leczyme as a result of introducing an expression vector encoding the leczyme into the cell. Leczyme-expressing cells can be obtained from in vivo sources by methods well known in the art such as mechanical disruption of tissue or digestion of tissue by enzymes to release cells from their surrounding matrix (see for example, Freshney *Culture of Animal Cells* (Alan R. Liss, New York, 1993), which is incorporated herein by reference). A leczyme-expressing cell can be a cell line that is available from public cell repositories such as from the American Type Culture Collection.

It is well known in the art that the binding between two molecules can be performed when either of the two molecules contains a detectable label. Thus, the identification of a detectably labelled carbohydrate ligand that binds to a leczyme attached to a solid support or a cell also can be performed if the leczyme contains the detectable label and the carbohydrate ligand is attached to a solid support or expressed by a cell. A leczyme can be detectably labelled using methods for labelling a protein, which are well know in the art and include, for example, biotinylation or incorporation of radioisotopic labelled precursors. A carbohydrate ligand-expressing cell can be a cell obtained from tissues or organs or can be a cell line such as a cell line available from a public repository.

Methods for attaching a carbohydrate ligand to a solid support depend on the chemical nature of the ligand. Thus, attachment can be accomplished through the carbohydrate moiety or other molecule bonded to the carbohydrate ligand attachment via chemistry suitable for attaching carbohydrate, peptide or lipid structures to a solid support. Methods to attach carbohydrates, proteins or lipids to various types of solid supports are well known in the art.

The binding of a carbohydrate ligand to a leczyme can be determined without the need for a detectable label by measuring a physical characteristic of the either the ligand or the leczyme such as absorption of ultraviolet radiation. Such methods for quantitating a protein or carbohydrate by physical characteristics are well known in the art. The ability to follow a physical characteristic of the ligand or leczyme can be applied to binding assays that use a solid support or an expressing cell or when both molecules are in solution. The binding of a carbohydrate ligand to a leczyme also can be evaluated if the ligand is a substrate for the enzymatic activity of the leczyme. In this case, binding can be measured by following substrate conversion kinetics measured, for example, by the Michealis-Menten equation (Devlin, *Textbook of Biochemistry* (Wiley-Liss Inc. New York, 1992), which is incorporated herein by reference).

Methods for identifying a carbohydrate ligand that binds a leczyme can be performed using a single purified carbohydrate ligand or a limited number of carbohydrate ligands, which can be purified by conventional procedures as described above or can be purified by binding to a reagent. A purified carbohydrate ligand can also be detectably labelled by methods disclosed herein. A carbohydrate ligand that is not purified, such as one that is in a sample containing other molecules, can be used in a binding assay provided it is attached to a solid support or is expressed by a cell and binding is determined by detecting binding of a leczyme. In this case, if the non-purified carbohydrate ligand can bind the leczyme, the sample containing the ligand can be subjected to purification and subsequent binding assays to obtain the carbohydrate ligand in a purified state.

Purified leczymes can be obtained from cells by classical methods for protein or glycoprotein purification such as methods known in the art for purifying class I or class II molecules. Leczymes also can be obtained from cells that have been modified by molecular biological techniques to enable expression of a leczyme. A gene encoding a leczyme can be cloned into an expression vector and then introduced into a host cell. Vectors are well known in the art and include, for example, cloning vectors and expression vectors, as well as plasmids or viral vectors (see, for example, Goedell, *Methods in Enzymology*, vol. 185 (Academic Press, New York, 1990), which is incorporated herein by reference). A baculovirus vector is an example of a vector that can be used to express a leczyme in insect cells and result in expression of new carbohydrate ligands on the cell.

A vector comprising a nucleic acid molecule encoding a leczyme also can contain a promoter or enhancer element, which can be constitutive or inducible and, if desired, can be tissue specific. Host cells also are known in the art and an appropriate host cell can be selected for the particular vector to be used. For example, a baculovirus transfer vector can be used with baculovirus DNA to infect insect cell lines such as SF21 cells. Cloning of such transformed cells to produce a stable cell line can provide a source of the expressed leczyme or can provide a source of carbohydrate ligand modified by the expressed leczyme.

The gene encoding a leczyme can be expressed as a fusion protein to assist in purification or in further downstream processing of the leczyme. For example, the leczyme can be produced as a chimeric protein fused to the CH2 or CH3 domain that constitutes the Fc binding region of an immunoglobulin molecule, as was performed previously for expressing the CD22β lectin (Stamenkovic et al. *Cell*, 66:1133–1144 (1991)). The use of Protein A from Staphylococcus aureus bound to a solid support, which is readily available from commercial sources, can be used to purify the Fc containing chimeric leczyme. In addition, the solid support containing the chimetic leczyme can be used directly to evaluate binding of a carbohydrate ligand.

The present invention provides methods to identify a leczyme that binds a carbohydrate ligand. In this method, a sample containing a leczyme is contacted with a carbohydrate ligand suspected of binding to the leczyme under suitable conditions to allow specific binding of the ligand to the leczyme. The methods that have been described above for identifying a carbohydrate ligand that binds to a leczyme can also be used to identify a leczyme that binds to a carbohydrate ligand. Leczymes to be identified for binding include, for example, a purified leczyme or a leczyme contained within a complex mixture such as a mixture of proteins expressed from a cDNA expression library. Methods to produce a cDNA expression library are well known in the art (see, for example, Sambrook et al, *Molecular Cloning: A laboratory manual* (Cold Spring Harbor Laboratory Press 1989), which is incorporated herein by reference).

The present invention provides methods of purifying a carbohydrate ligand that specifically binds to a reagent. In these methods, a sample containing the carbohydrate ligand is contacted with the reagent under suitable conditions to allow formation of a ligand-reagent complex. Suitable conditions includes, for example, an appropriate buffer concentration and pH and time and temperature that permits binding of the carbohydrate ligand to the reagent. The ligand-reagent complex is then separated from the rest of the sample by a separation method such as by washing, and the ligand is dissociated from the complex.

As used herein, "reagent" means a chemical or biological molecule that can specifically bind to a carbohydrate ligand. For example, a leczyme that binds to a carbohydrate ligand is a reagent that can be used to purify that ligand. Also, an antibody can be a reagent if it can react specifically with the carbohydrate, protein or lipid portion of a carbohydrate ligand.

Purification of the carbohydrate ligand can be accomplished if the reagent is attached to a solid support such as agarose, Sepharose or plastic. Methods for coupling a protein or a carbohydrate to a solid support, disclosed above for detecting the binding of a carbohydrate ligand to a leczyme, also are useful for attaching a reagent to a solid support.

Methods to dissociate a carbohydrate ligand from a ligand-reagent complex can depend on the nature of the reagent. For example, if the reagent is a leczyme, then a method for dissociating the complex can involve competitive inhibition of the complex with a sugar structure that has binding affinity for the same site in the leczyme that binds the carbohydrate ligand. Other well known treatments that are useful for dissociating a carbohydrate ligand from a reagent include, for example, extremes in pH, high salt concentration or chaotrophic agents (see, for example, Harlow and Lane, supra, 1988), which is incorporated herein by reference and Varki, supra, 1994). Carbohydrate ligands purified by the above disclosed methods are suitable for structural analysis as described above, in order to enable future production of the ligand by chemical or enzymatic synthesis.

An antibody that specifically binds to a carbohydrate ligand can be produced to the carbohydrate or a protein moiety or a lipid moiety, if such moieties are bonded to the ligand. An antibody specific for the peptide backbone of carbohydrate ligand such as the peptide backbone of a mucin can be useful for purifying a source of mucin from different cells or from different individuals, since the peptide backbone can be more conserved between peptide containing carbohydrates than the carbohydrate portions of these molecules. Methods for producing antibodies such as polyclonal antibodies, monoclonal antibodies, antibody fragments or the like, that are specific for protein, carbohydrate or lipid are well known in the art (see, for example, Harlow and Lane supra, 1988).

The present invention provides methods for purifying a leczyme that specifically binds to a carbohydrate ligand. In these methods, a sample containing the leczyme is contacted with a carbohydrate ligand under suitable conditions to allow formation of a ligand-leczyme complex. Suitable conditions includes, for example, an appropriate buffer concentration and pH and time and temperature that permits binding of the leczyme the carbohydrate. The ligand-reagent complex is then separated from the rest of the sample by a method such as by washing, and the leczyme is dissociated from the complex.

Purification of the leczyme can be accomplished if the carbohydrate ligand is attached to a solid support such as agarose, Sepharose or plastic. Methods for coupling a carbohydrate ligand to a solid support, such as those disclosed above for detecting the binding of a carbohydrate ligand to a leczyme, are useful for attaching a carbohydrate ligand to a solid support. Methods for dissociating the leczyme from the ligand-leczyme complex can utilize the methods disclosed herein for dissociating a carbohydrate ligand from a ligand-leczyme complex.

The present invention provides methods to identify a carbohydrate ligand that modifies the function of a leczyme-expressing cell by contacting a sample containing a carbohydrate ligand with the cell under suitable conditions, which allow specific binding of the ligand to the leczyme on the cell. After a suitable period of time to allow for binding of the ligand to the leczyme, the cells are evaluated to determine their function. A carbohydrate ligand that modifies the function of a leczyme-expressing cell is one that when contacted with the cell results in a function that differs from the function of the same type of cell that had not contacted the ligand.

As used herein, "function" in reference to a cell includes any activity that can be detected for a cell. The function of a cell can vary with the nature of the cell in question. For example, the function of a T lymphocyte can include activities such as the production of certain cytokines, acquisition of cell mediated lympholysis, ability to mediate antibody dependent cell mediated cytotoxicity or the ability to help B lymphocytes to produce antibody. Thus, a particular carbohydrate ligand that can bind to a leczyme on a T lymphocyte and subsequently effect the function of the cell can do so by increasing or decreasing any of the above T lymphocyte functions.

Contacting a carbohydrate ligand with a leczyme-expressing cell can be performed in vitro in a cell culture medium. Methods for measuring the function of lymphoid cells or other cells are well known in the art (see for example, Colligan et al., *Curr. Protocols in Immunol.* (Greene Publishing Associates and Wiley Interscience, New York, 1992); Mishell and Shiigi, *Selected Meth. in Cell. Immunol.* (W. H. Freeman and Co., New York, 1980), each of which are incorporated herein by reference).

The present invention also provides methods to identify a leczyme that modifies the function of a carbohydrate ligand-expressing cell. Methods described above for identifying a carbohydrate ligand that modifies the function of a leczyme-expressing cell are also useful for identifying a leczyme that modifies the function of a carbohydrate ligand-expressing cell.

The present invention provides methods to modify the function of a leczyme-expressing cell by contacting the cell with a carbohydrate ligand that binds the leczyme. In addition, the invention provides methods to modify the function of a carbohydrate ligand-expressing cell by contacting the cell with a leczyme that binds the ligand. The identification of either a carbohydrate ligand or a leczyme that can modify the function of a cell has both in vitro and in vivo uses. For example, ligands or leczymes capable of decreasing or increasing the functional activity of cell that is involved in a disease state can be administered to an individual to treat the disease.

The present invention provides methods to identify a peptide that can bind to the carbohydrate ligand binding-site of a leczyme. These methods involve contacting a sample containing a peptide or peptides to be tested with a leczyme under suitable conditions to enable binding of peptide to the leczyme. Subsequently, the leczyme is reacted with a carbohydrate ligand known to bind to the leczyme. The reaction is performed under conditions suitable for the carbohydrate ligand to bind to the leczyme. Alternatively, the peptide, leczyme and carbohydrate ligand can be added together at the start of the reaction.

The carbohydrate ligand can be added directly to the mixture containing the peptide and leczyme or can be added after any unbound peptide has been removed from the leczyme. After the end of the reaction, the amount of carbohydrate that bound to the leczyme is determined and compared to the amount of carbohydrate ligand that bound to leczyme in a control sample that did not contain peptide. If the amount of carbohydrate ligand that bound to the leczyme in the sample containing peptide is less than the amount of carbohydrate ligand that bound to the leczyme in the control sample, then it can be concluded that the peptide had bound to the carbohydrate ligand binding site of the leczyme and is therefore a peptide mimetope of the carbohydrate ligand.

A peptide mimetope can be identified in an assay format that utilizes a carbohydrate ligand containing a detectable label and a leczyme that is bound to a solid support or is expressed by a cell. Methods disclosed herein for identifying a carbohydrate ligand that bind to a leczyme are useful to generate the assay format for identifying a peptide mimetope of a carbohydrate ligand.

A defined peptide sequence can be chemically synthesized or produced by biological methods, such as by recombinant DNA techniques (see, for example, Sambrook et al., supra, 1989). A complex mixture of peptides also can be used to identify a peptide mimetope. Such complex mixtures can include, for example, a mixture of defined sequences, or can be a semi-random or random library of sequences. Methods to generate peptide libraries by such methods as chemical synthesis on a bead or a microtiter plate or biological production such as on the surface of a bacteriophage are well known in the art (see, for example, Huse et al., *Science* 246:1275–1281 (1989), which is incorporated herein by reference).

A peptide that can bind to the carbohydrate ligand binding site of a leczyme can also have some of the functional characteristics of a carbohydrate ligand and thus be considered a functional mimetope of the carbohydrate ligand. Such peptide mimetopes can be used to modify the function of a cell and also can be used to treat a disease state that involves a leczyme that can bind to the mimetope.

The present invention provides methods to modify a cell to produce a carbohydrate ligand, comprising introducing an expression vector encoding a leczyme into a cell to obtain expression of the leczyme, which results in production of the carbohydrate ligand by the cell. Cells producing a particular carbohydrate ligand are useful to provide unique types of ligands, which can be purified from the cells. In addition, such cells are useful in binding assays to identify a leczyme that binds the ligand.

The present invention provides methods for modulating an immune response in an individual, such as a human or other animal, using an antigen for which the immune response is desired and a carbohydrate ligand that binds to a leczyme. As leczymes include, for example, the major histocompatibility complex molecules, that are involved in presentation of foreign molecules for recognition by cells of the immune system, injection of a carbohydrate ligand and an antigen can modulate an immune response. A used herein, "modulate" means increase or decrease. An increase in the immune response can be obtained by administering a carbohydrate ligand bound to antigen such that the antigen is targeted via the leczyme to an antigen presenting cell.

An antigen can be associated with a carbohydrate ligand by covalently bonding the antigen to carbohydrate or to any protein or lipid of the ligand using methods well known in the art. The actual method to covalently couple the antigen to the carbohydrate ligand will depend on the nature of each molecule to be coupled and whether the coupling procedure is detrimental to the any critical antigenic determinants of the antigen or the capability of the carbohydrate ligand to bind its' target leczyme. Such detrimental effects can be readily evaluated in binding assays as described above.

More than a single antigen molecule or more than a single carbohydrate ligand can be coupled together to produce an immunogen. Such molecules can be made multivalent for either or both of the antigen or the carbohydrate ligand and can be used for eliciting a greater immune response than an immunogen containing a single molecule of antigen and a single molecule of a carbohydrate ligand.

Methods to increase an immune response in an individual are well known to those in the art and require optimization of parameters such as dose, route of administration, use of an adjuvant, or schedule of administration (see, for example, Harlow and Lane, chapter 5, supra, 1988). An increased immune response obtained after administering an antigen and a carbohydrate ligand is achieved when the immune response parameter has increased by a statistically significant level over the level of the parameter manifested prior to administration of the antigen and carbohydrate ligand.

The immune response parameters that can increase after administering an antigen associated with a carbohydrate ligand include an antibody-mediated response or a cellular-mediated response. Methods to measure antibody immune responses are well known to those in the art and include, for example, detection of immunoglobulins by both in vitro and in vivo methods (see for example Harlow and Lane, supra, 1988). Methods to measure cellular immune responses are also well known in the art and include in vivo methods such as skin testing for delayed hypersensitivity and in vitro methods such as direct cell cytotoxicity or cell activation assays (see, for example, Coligan et al. supra, 1992; Mishell and Shiigi, supra, 1980).

An antigen associated with a carbohydrate ligand can be used to decrease an immune response to the antigen and can be particularly useful for treating a deleterious immune response such as an autoimmune disease state. Methods for decreasing an immune response can, under some conditions result in a prolonged state of specific immunological unresponsiveness to the antigen, commonly referred to as a state of tolerance to the antigen.

Decreasing an immune response to an antigen by administering the antigen bonded to a carbohydrate ligand can be accomplished using methods well known in the art to suppress or tolerize an individual to an antigen. Such methods include, for example, administration of low doses, monomeric and nonaggregated forms of the antigen and carbohydrate ligand or administration orally. In addition, a decreased immune response can be obtained by administering the antigen and carbohydrate ligand concurrently with an immunosuppressive agent such as cyclosporin A, FK506 or antibodies to a particular T lymphocyte cell-surface receptor. Methods for using such agents to decrease the immune response to an antigen in humans or animals are well known in the art.

The present invention provides methods for treating a disease state involving a leczyme, by administering an effective amount of a carbohydrate ligand that binds to the leczyme. As used herein, the term "disease state" includes any diseases, whether genetic or acquired, provided a leczyme plays a role in the disease process. Such disease states include inflammation, transplantation rejection, and also includes diseases having both a genetic and an environmental basis such as iron storage diseases, autoimmunity or cancer. In addition, a disease state includes diseases resulting from an infectious agent such as a virus, bacteria, yeast or parasite. The ability of an infectious agent to enter and infect cells of the host can occur by binding to leczyme or carbohydrate ligand expressed on the cells of the host. A peptide mimetope for a carbohydrate can also be used to treat a disease state that involves a leczyme for which the mimetope can bind.

The present invention provides methods for treating a disease state involving a leczyme by administering a leczyme having a similar binding specificity for a carbohydrate ligand as the leczyme involved in the disease state. The disease states useful for treatment by a leczyme include those described above for treatment by a carbohydrate ligand. Thus, aberrant self-recognition, mediated by a leczyme in a diseased individual, can be treated by administration of a leczyme. Such a leczyme can bind to the natural carbohydrate ligand detected on a target cell by the aberrant self-reactive leczyme-expressing cell, and, therefore, block the ability of the self-reactive leczyme-expressing cell to recognize and react aberrantly towards the target cell.

The present invention provides methods for treating an iron metabolic disorder known as hemochromatosis. Defects in iron metabolism can have a basis in leczyme function. In elevated concentrations, iron is a toxic inorganic molecule that has been implicated in the pathophysiology of a number of common diseases. These include but are not limited to cancer (Stevens et al, *N. Engl. J. Med.*, 319:1047 (1988); Stevens, et al., *Med. Oncol. Tumor Pharmacother*, 7:177–181 (1990)), heart disease (Kannel, et al, 1976; Sullivan, *Lancet*, 1:1293–1294 (1981); Salonen, et al, *Circulation*, 86:803–811 (1992)), reperfusion injury (Zweier, *J. Biol. Chem.*, 263:1353–1357 (1988)) and rheumatoid arthritis (Blake et al., *Arthritis Rheum.*, 27:495–501 (1984)). There is no argument that severe iron overload results in a constellation of pathologies, collectively called hemochromatosis, the most common genetic disease affecting man.

Hemochromatosis results from enhanced absorption of iron from the GI tract by active transport but the underlying metabolic defect is currently unknown. Identification of the genes responsible for the absorption of iron, and developing an animal model in which iron overload is due to active enhanced absorption of iron from the GI tract, would greatly facilitate understanding hemochromatosis and increase knowledge about the general mechanisms of iron metabolism. The present invention provides the results from a new animal model and data from humans that indicate a role for an MHC-encoded leczyme in the pathogenesis of hemochromatosis.

Hemochromatosis is not usually brought to clinical attention until symptoms develop, and several studies have indicated that removal of the iron after the development of tissue damage does not necessarily improve the organ function (Cundy, et al., *Clin. Endocrinol.*, 38:617–620 (1993); Westera et al., *Am. J. Clin. Path.*, 99:39–44 (1993)). Hemochromatosis is an underdiagnosed and undertreated disease that would benefit greatly from early diagnosis and an effective treatment (for reviews see Edwards et al., *Hosp. Pract. Suppl.*, 3:30–36 (1991); Edwards and Kushner, *N. Engl. J. Med.*, 328:1616–1620 (1993)).

Untreated hemochromatosis is characterized by iron overload of parenchymal cells, which is toxic and the probable cause of various complications including hepatopathy (including cirrhosis, and liver cancer), arthropathy, hypogonadotropic hypogonadism, marrow aplasia, skin disorders, diabetes mellitus, and cardiomyopathy (for review see Halliday and Powell, *Iron and Human Disease*, Lauffer, RB, (ed). 131–160 (1992)). There are reportedly 1.5 to 2 million active cases of hemochromatosis within the U.S., with approximately 25% of late diagnosed or untreated patients developing hepatomas.

In untreated hemochromatosis, iron is universally deposited in the hepatocytes of the liver, and elevated saturation of transferrin with elevated serum ferritin levels combined with liver biopsy provides the best diagnostic test currently available (Fairbanks, *Hosp. Pract.*, 26:17–24 (1991)). The iron is found primarily in the cytoplasm of hepatocytes, and by electron microscopy in lysosomal vacuoles, and in more severe cases, iron is deposited in mitochondria (for review see Iancu, *Pedo Pathol.*, 10:281–296 (1990)). Other liver toxins such as alcohol and hepatitis exacerbate the damage caused by the iron deposition (Piperno et al., *J. Hepat.*, 16:364–368 (1992)). Patients with hemochromatosis are advised not to drink alcohol, because of increased liver damage, or to smoke tobacco products, as iron deposition can also occur in the lungs.

Hemochromatosis is an autosomal recessive disease in which the responsible gene(s) is linked to the A locus of the human MHC (HLA complex), located on human chromosome 6 (Simon and Brissot, *Hepatol.*, 6:116–124 (1988)). Linkage to human HLA-A3 has been documented in approximately 73% of cases. However, other genetic loci also have been implicated, especially in African (Gorduke et al., *N. Engl. J. Med.*, 326:95–100 (1992)) and African-American populations (Barton et al., *Blood,* 85:95a (1993)).

Hemochromatosis is the most common genetic malady in humans far exceeding cystic fibrosis, phenylketonuria and muscular dystrophy combined (Leggett et al., *Clin. Chem.*, 36:1350–1355 (1990)). One explanation for the high incidence of this genetic disease may be that results from different mutations in multiple linked genes that produces a similar phenotype. Hemochromatosis occurs most frequently in populations of European origin with a frequency in homozygotes and heterozygotes of approximately 0.3 and 13%, respectively.

Several markers, including the recently described D6S105, have been identified in the human MHC locus and have narrowed the genomic location of the hemochromatosis gene to within 1 centimorgan of the A locus (Jazwinska et al., *Am. J. Hum. Genet.*, 53:347–352 (1993)), and possibly centromeric to HLA-F (Gasparini, et al., *Hum. Mol. Genet.*, 5:571–576 (1993)). Others have reported candidate (HC) genes located 20–200 kb telomeric to HLA-A (el Kahloun et al., *Hum. Mol. Genet.*, 2:55–60 (1993)). While several of these candidate genes were thought to be single copy, three of the genes, termed HCG II, IV and VII, were found to be multicopy genes. Thus, despite the advances made in determining the location of the HC gene, it has not yet been isolated.

Animal models for iron overload exist, however, these models are not entirely suitable for the study of hemochromatosis since they do not reflect enhanced iron absorption from the gut by active transport. Mice homozygous for deletion of the gene encoding $\beta_2$M ($\beta_2$-/-mice (Koller et al., *Science*, 248:1227–1230 (1990); Zijlstra et al., *Nature*, 344:742–746 (1990)) provide an excellent animal model for the study of hemochromatosis. These animals lack detectable class I proteins on the cell-surface, although biochemical labeling shows that class I gene products are being synthesized. Activated lymphocytes from $\beta_2$-/- animals can be lysed by activated natural killer (NK) cells, again suggesting a deficiency in class I expression (Liao et al., *Science*, 253:199–202 (1991)). These mice were originally developed to study the role of $\beta_2$M in development. While the mice developed and bred normally, they failed to generate significant numbers of CD8+ T cells. Consequently, these mice have been intensely studied from an immunologic perspective.

$\beta_2$-/-mice combat viral infections relatively well, although the course of the infection is longer than in normal animals (Eichelberger et al., *J. Exp Med.*, 174:875–878 (1991); Muller et al., *Nature*, 255:1576–1579 (1992)). They reject allografts (Zijlistra et al., *J. Exp. Med.*, 175:885–889 (1992)) and show higher levels of Ig production and faster class switching of antibody types than normal mice. Although CD8+ T cells are low to undetectable at birth, studies have shown that the animals can generate CD8+ T cells, and a cytotoxic CD8+ T cell response can be mounted under appropriate circumstances (Apasov and Stikovsky, *J. Immunol.*, 152:2087–2097 (1994)). Another significant abnormality reported in these animals is that they develop hyperglycemia (glucose>300 mg/dl) in old age (greater than 2 years). It has been suggested that the onset of diabetes in the $\beta_2$-/- mice is related to autoimmunity (Faustman et al., *Science*, 254:1756–1761 (1991)), however this explanation has been disputed (Serreze et al., *Diabetes*, 43:505–509 (1994); Wicker et al., *Diabetes*, 43:500–504 (1994)).

$\beta_2$-/-mice can develop iron overload that is similar to human hemochromatosis. $\beta_2$-/-mice can spontaneously develop hepatomas. This observation combined with the molecular biology data of the $\beta$-GAP genes (see Example I), suggested that the mice would develop iron overload. Histochemical examination of tissues from these mice, confirmed this hypothesis. Iron was found deposited in the liver of all animals, and in the kidneys, spleen and lungs of some of the animals. In addition, 16% of the animals developed liver disease, having either hepatomas or liver necrosis. Thus, the clinical findings for the $\beta_2$-/- deficient mice are sufficiently similar to the pathology of hemochromatosis to make the $\beta_2$-/-mouse an attractive model for the study of a mechanism underlying human hemochromatosis. More importantly, the $\beta_2$-/-mice demonstrate that $\beta_2M$ plays a role in this disease.

The ability of β-GAP promoters to co-regulate both the β-GAP gene and a nonclassical class I gene that encodes leczyme, both of which are expressed in the intestine, supports a role for a class I leczyme in hemochromatosis. The nonclassical class I gene regulated by the β-GAP promoter is a leczyme that can recognize and modify a carbohydrate structure associated with the β-GAP gene product, the latter of which directly or indirectly binds iron (ie. β-GAP can be an iron carrier). Disruption of $\beta_2M$ expression results in a loss of regulation of the leczyme function provided by the nonclassical class I molecule, leading to iron overload and hemochromatosis.

A carbohydrate ligand or a leczyme of the present invention can be used to prepare a medicament for the treatment of a disease state such as hemochromatosis, autoimmune disease, transplantation rejection, inflammation or infection. Autoimmune diseases that can be treated by the present invention include systemic autoimmune diseases such as ankylosing spondylitis, multiple sclerosis, rheumatoid arthritis, slceroderma, Sjögren's syndrome or systemic lupus erythematosus, and organ-specific autoimmune diseases such as Addison's disease, Goodpasture's syndrome, Grave's disease, Hashimoto's thyroiditis, idiopathic thrombocytopenia purpura, myasthenia gravis or pernicious anemia. As hemochromatosis in humans is likely mediated by a β-GAP promoter-driven leczyme, then treatment with a carbohydrate ligand, leczyme or competing molecule with the same or similar binding specificity as the leczyme involved in the disease can be used to modulate the disease process. A carbohydrate ligand that binds the nonclassical class I leczyme involved in hemochromatosis can be administered to inhibit binding to the β-GAP iron carrier.

A process to follow for using a carbohydrate ligand to treat a disease such as autoimmunity can first require identification of the lecyzme that is involved in the disease process. Subsequently, a candidate carbohydrate ligand that can bind to the leczyme is identified by methods disclosed herein. Thus, such candidate carbohydrate ligands can then be tested in vitro to identify those efficient at blocking the autoimmune reaction exhibited when the leczyme on autoreactive immune cells from the diseased individual recognizes a carbohydrate molecule expressed on the cells of the individual that is the target of the autoreactive cell. The autoimmune reaction can be measured by an increase in a cell function such as cell proliferation or release of cytokines (see for example, Coligan et al. supra, 1992; Mishell and Shiigi, supra, 1980). The best candidate carbohydrate ligands can then be used as a medicament to treat the disease.

The methods disclosed herein for the treatment of hemochromatosis are also suitable for the treatment of many other medical diseases or complication resulting from iron overload. Since multiple leczyme genes are involved in mediating control of iron metabolism, the type of mutation, its location in the gene and the number and type of leczyme genes mutated in an individual are factors that can effect the extent of iron overload in an individual. As the extent of iron overload exhibited by an individual is dependent on the above factors, then the methods disclosed herein to treat hemochromatosis are also applicable for treating other diseases resulting from iron overload. Such diseases include, for example, hepatopathy (including cirrhosis, and liver cancer), arthropathy, hypogonadotropic hypogonadism, marrow aplasia, skin disorders, diabetes mellitus, and cardiomyopathy (for review see Halliday and Powell, *Iron and Human Disease*, Lauffer, RB, (ed). 131–160 (1992)).

In order to modulate hemochromatosis or other iron storage disease, the carbohydrate ligand or mimetope is administered in an effective amount. The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of carbohydrate ligand required to obtain an effective dose in a subject depends on many factors including the age and general health of the subject as well as the route of administration and the number of treatments to be administered and the chemical form of the carbohydrate ligand. In view of these factors, the skilled artisan would adjust the particular amount so as to obtain an effective amount for the subject being treated.

A carbohydrate ligand or a leczyme also is useful in vivo for the treatment of autoimmune diseases involving a leczyme. In autoimmune disease, a leczyme expressed on a lymphoid cell can recognize a self-carbohydrate ligand as a foreign carbohydrate ligand, resulting in immune-directed destruction of cells expressing the self-carbohydrate ligand. Thus, administration of a carbohydrate ligand, mimetope or other competing molecule that can bind to the leczyme involved in aberrant self-recognition can block lymphoid cell recognition or activation leading to a reduction in symptoms or cessation of autoimmune disease. Alternatively, administration of a leczyme that has the same or similar binding specificity for the self-carbohydrate ligand recognized by a leczyme of the autoreactive lymphoid cell can also be used to treat the autoimmune disease.

A carbohydrate ligand or a leczyme can be used to treat a disease state resulting from an infectious agent such as a virus, bacterium, yeast or parasite. Infectious agents have evolved to express their own external receptors that can recognize carbohydrate structures or leczymes on the cell-surface, enabling entry of the agent into the cell to be infected. Thus, administration of an appropriate carbohydrate ligand or a leczyme to an individual exposed to an infectious agent can block the binding of the agent to target cells, subsequently inhibiting the extent of infection and thereby reducing the spread of the disease.

A carbohydrate ligand or a leczyme of the present invention can be used to treat transplantation rejection. Since rejection is based on the recognition of foreign molecules by lymphocytes of the transplant recipient, then treatment with a carbohydrate ligand that can bind to the leczyme of the transplant recipient's lymphocyte that is involved in foreign antigen recognition can inhibit recognition leading to transplantation rejection. Also, administration of a leczyme that has the same or similar binding site specificity as the leczyme of a transplant recipient's lymphocyte involved in foreign antigen recognition can inhibit recognition leading to transplantation rejection.

A carbohydrate ligand or leczyme of the present invention is particularly useful when administered as a pharmaceutical composition containing a pharmaceutically acceptable carrier. Pharmaceutically acceptable carriers are well known in the art and include, for example, aqueous solutions such as a physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of a carbohydrate ligand or leczyme. Such physiologically acceptable compounds include, for example, carbohydrates, such as glucose, sucrose, dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition.

One skilled in the art would know that a pharmaceutical composition containing a carbohydrate ligand or leczyme can be administered to a subject by various routes including, for example, by direct instillation, orally or parenterally, such as intravenously, intramuscularly, subcutaneously or intraperitoneally. The composition can be administered by injection or by intubation. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla., 1984), which is incorporated herein by reference). Liposomes, for example, which consist of phospholipids or other lipids, are nontoxic, physiologically acceptable and metabolizable carriers that are relatively easy to make and administer.

An expression vector encoding a leczyme can be administered in vivo to treat a disease state resulting from a leczyme. For example, a disease state resulting from a mutated leczyme, such as anemia, can be treated by administering an expression vector encoding a functional leczyme involved in iron transport and obtaining expression of the vector in cells of the digestive tract.

The level of expression of a particular leczyme in a cell can have a impact on the nature of a carbohydrate ligand expressed by the cell. If expression of a particular carbohydrate ligand is involved in a disease process, the ligand can be eliminated from a cell by reducing the expression of the leczyme responsible for producing the ligand. Thus, an expression vector can contain an exogenous nucleic acid molecule encoding an antisense nucleotide sequence that is complementary to a nucleotide sequence encoding a portion of a leczyme such that when introduced into a cell under the appropriate conditions, the expression vector can produce an antisense nucleic acid molecule, which can selectively hybridize to the leczyme gene or message in a cell and, thereby, affect the expression of the leczyme in the cell. For example, the antisense nucleic acid molecule can hybridize to a leczyme gene in the cell and can reduce or inhibit transcription of the leczyme gene. Also, the antisense molecule can hybridize to the message encoding the leczyme in the cell and can reduce or inhibit translation, processing and cell stability or half-life of the RNA.

Expression vectors also can be used to effect the expression of a leczyme or of a carbohydrate ligand involved in a disease state by introducing into a cell an exogenous nucleic acid molecule encoding a ribozyme that can specifically cleave RNA encoding the leczyme or peptide backbone of a carbohydrate ligand. Thus, by introducing the ribozyme into cells involved in a disease process, one can reduce expression of the leczyme or carbohydrate ligand involved in the disease and therefore reduce or inhibit the disease process. An antisense nucleic acid molecule or a ribozyme can be chemically synthesized and incorporated into an expression vector using recombinant DNA techniques. The antisense nucleic acid molecule or ribozyme also can be added directly to a cell without having been incorporated into an expression vector.

Methods for introducing an expression vector into cell are well known in the art. Such methods are described in Sambrook et al, supra, 1989; Kriegler M. *Gene Transfer and Expression: A Laboratory Manual* (W. H. Freeman and Co. New York N.Y. (1990), both of which are incorporated herein by reference) and, for example, include transfection methods such as calcium phosphate, electroporation, lipofection, or viral infection.

Recombinant viral vectors are available for introducing an exogenous nucleic acid molecule into a mammalian cell and include, for example, adenovirus, herpesvirus and retrovirus-derived vectors. For example, a viral vector encoding a leczyme can be packaged into a virus to enable delivery of the genetic information and expression of these leczyme in gastrointestinal epithelial cells following infection by the virus. Also, a recombinant virus which contains an antisense sequence or a ribozyme specific for a nucleotide sequence encoding a leczyme can introduced into a cell in an individual to inhibit a disease state mediated by the leczyme or a leczyme with a similar carbohydrate binding specificity.

Recombinant viral infection can be more selective than direct DNA delivery due to the natural ability of a virus to infect only certain types of cells. This natural ability for selective vital infection can be exploited to limit infection to only certain cell types within a mixed cell population. For example, adenoviruses can be used to restrict viral infection principally to cells of epithelial origin. In addition, a retrovirus can be modified by recombinant DNA techniques to enable expression of a unique receptor or ligand that provides further specificity to viral gene delivery. Retroviral delivery systems that provide high infection rates, stable genetic integration and high levels of exogenous gene expression are well known in the art.

As described above, recombinant viral delivery systems exist that provide the means to deliver genetic information into a selected type of cell. The choice of viral system will depend on the desired cell type to be targeted, while the choice of vector will depend on the intended application. Recombinant viral vectors are readily available to those in the art and can be easily modified by one skilled in the art using standard recombinant DNA methods (see, for example, Krieger, *Gene Transfer and Expression: A Laboratory Manual*, (W. H. Freeman and Company, 1990); Goeddel, *Methods in Enzymology*, vol. 185, (Academic Press, 1990); and Stoker, In *Molec. Virol., A Practical Approach* (eds. Davison and Elliott, IRL Press, 1993), all three of which are incorporated herein by reference).

The present invention provides methods for diagnosing a genetic predisposition for hemochromatosis or other iron storage diseases based on a leczyme by detecting a mutation in the heavy chain of a class I MHC molecule encoded for by a gene in the MHC locus. These methods can be used to diagnose an individual having the symptoms of an iron storage disease. A positive diagnosis of mutation in an individual's heavy chain is useful to verify the underlying cause of the disease and by identifying the particular leczyme that is mutated. The identification of the mutated leczyme can be used with the methods disclosed herein to identify a carbohydrate suitable for treating the disease.

An individual who does not have an iron storage disease, but is suspected of inheriting a mutation that can predispose the individual to develop an iron storage disease later in life can also benefit from having their class I molecules tested for mutation by the methods disclosed herein.

A mutation that is diagnostic for the disease is one that results in a significantly reduced affinity of the heavy chain for human $\beta_2$M. For example, a mutation in a nonclassical class I heavy chain that results in deletion of a signal for phosphorylation is a mutation that is diagnostic for hemochromatosis since a properly phosphorylated heavy chain is necessary for the chain to interact with $\beta_2$M. Consensus amino acid sequences that signal a cell to phosphorylate a serine or a threonine residue in a polypeptide are well known in the art. A mutation that is diagnostic for hemochromatosis also can occur in a region of the heavy chain that is near to a phosphorylation site. Such a mutation can reduce the ability of the heavy chain to associate with $\beta_2$M if the phosphate group added to this site cannot be removed in a cell.

Methods to detect a phosphorylation site mutation in a nonclassical class I heavy chain can be based either on analysis of the protein or the nucleic acid encoding the protein. For protein determination, the nonclassical class I molecule can be purified from a source of cells or body fluids of an individual and the heavy chain can be isolated from $\beta_2$M. Methods to purify a class I MHC molecule and isolate the heavy chain from $\beta_2$M are well known in the art. The isolated heavy chain can then be subjected to amino acid sequencing, peptide mapping or other such protein analyses to determine if the sequence a phosphorylation site has been mutated. Such methods for protein determination are well known to those in the art.

A mutation in a nucleic acid sequence can be detected by various methods to analyze nucleic acids such as by nucleic acid sequencing, polymerase chain reaction or hybridization. Such methods are well known to those in the art (see, for example, Sambrook et al, supra, 1989; Hames and Higgins *Nucleic Acid Hybridisation: a practical approach* (IRL Press, New York, 1985), both of which are incorporated herein by reference).

Methods to detect decreased binding of a mutated heavy chain with $\beta_2$M can be used for diagnosing an iron storage disease such as hemochromatosis. In these methods, the heavy chain of an class I MHC molecule is isolated from an individual and contacted with $\beta_2$M under conditions suitable for a non-mutated such heavy chain to associate with $\beta_2$M. A control reaction, which contains a non-mutant form of the same or similar class I heavy chain to the one being tested for a mutation is performed in parallel. After contacting the heavy chain with $\beta_2$M, the reaction is incubated under suitable conditions, including, for example, an appropriate buffer concentration and pH and time and temperature, which is sufficient for the control heavy chain to associate with $\beta_2$M. The heavy chain being tested from the individual is considered to have a mutation diagnostic for an iron storage disease when the fraction of this heavy chain that associates with $\beta_2$M is significantly less than the fraction of control heavy chain that associates with $\beta_2$M.

The association of a class I heavy chain with $\beta_2$M can be detected, for example, by attaching one of the molecules to a solid support and attaching a detectable label such as a radionuclide or a fluorescent label to the other molecule and measuring the amount of detectable label that is associated with the solid support, wherein the amount of label detected indicates the amount of association of the heavy chain with $\beta_2$M.

The following examples are intended to illustrate but not limit the present invention.

EXAMPLE I

CLONING AND EXPRESSION OF THE $\beta$-GAP GENES

This example provides an approach to identify and clone leczyme genes from various species of animal to elucidate their role in iron metabolic diseases.

Cloning of the Mouse $\beta$-Gap Genes

Genomic $\lambda$ libraries were constructed by partial Hae III digestion of DNA from A/J and Balb/c mouse liver and cloning the fragments into the vector Charon 4A. The libraries were screened with the S15 probe, isolated from the H-2L$^d$ gene (Margulies et al., *Nature*, 295:168–170 (1982), which is incorporated herein by reference)). S15 is a 3' class I MHC mouse probe and consists of 522 base pairs including 36 base pairs of exon 4 encoding the alpha-3 domain and 486 base pairs of intron (Evans et al., *Proc. Natl. Acad. Sci. (USA)*, 79:1994–1998 (1982)). Probes were prepared by excising the insert from M13 RF or pUC18, purifying the fragment from disulfide cross-linked acrylamide gels (Hansen, *Anal. Biochem.* 116:146–151 (1981)), and labeling with $^{32}$P to a specific activity of $>10^8$ cpm/μg by nick translation (Rigby et al., *J. Mol. Biol.* 113:237–251 (1977)). Libraries were screened using standard colony hybridization techniques (for details see Sambrook et al., supra, 1988).

Seventeen unique $\lambda$ clones were isolated from the libraries and were subjected to restriction enzyme digestion mapping. BamHI digestion and gel electrophoresis of these clones revealed five from the A/J strain and one from the Balb/c stain that contained a unique 500 base pair (bp) BamHI restriction fragment (BB500). The six clones containing the unique fragment were subjected to BAMH1 digestion, the BB500 fragment was gel purified and subcloned into M13 vector Mp18 and mp19 (Yanisch-Perron et al., *Gene* 33:103–119 (1985)). DNA sequences were determined by the chain termination method (Sanger, et al., *Proc. Natl. Acad. Sci. (USA)* 74:5463–5467 (1977)) using $^{35}$S-ATP. Reactions were analyzed on 6% urea-polyacrylamide gradient gels (Biggins et al., *Proc. Natl. Acad. Sci. (USA)* 80:3963–3965 (1983)). DNA sequences were assembled and analyzed using the University of Wisconsin Computer Group Programs (Devereux, et al., *Nucleic Acids Res.* 12:387–395 (1984)) run on a VAX-11/785 computer.

DNA sequence comparisons demonstrated that the BB500 fragments share greater than 93% sequence homology. A region within the BB500 fragment shows 100% sequence homology between the $\lambda$ clones and has been termed $\beta$-GAP (globin analogous promoter) since it is a regulatory motif that shares sequence homology with mouse, rabbit or human $\beta$-globin promoters (for a detailed comparison see ahead). There is close similarity between all six fragments (called $\beta$-GAP1–6) with the minor exception of $\beta$-GAP4 where an 8 base pair sequence AAGAGGAG, immediately downstream of a CCAAT element, has been deleted. There are other minor differences between these sequences, and the $\lambda$ clones they have been isolated from demonstrate different restriction patterns confirming that the various $\lambda$ clones contain unique sequences and are not a cloning artifact. Thus, the A/J strain mouse contains at least five highly homologous $\beta$-GAP sequences within its genome.

Mapping the $\beta$-GAP Sequences Map to Chromosome 17 in the Mouse

Southern blotting was used to determine if the BB500 sequence could identify genes located on chromosome 17 of the mouse. DNA from several Chinese hamster ovary (CHO) mouse somatic hybrid cell lines were evaluated by Southern blotting using the $\beta$-GAP6 BB500 probe. Genomic DNA was isolated from cultured cells, digested with EcoR1, electrophoresed on 0.8% agarose gels and transferred to a nitrocellulose membrane. Hybridization with the BB500 probe was carried out in the presence of dextran sulfate under the conditions described by Meinkof and Wahl (*Anal.*

*Biochem.* 138:267–284 (1985)) with a final wash in 0.2X sodium chloride sodium citrate buffer, pH 7.0 (SSC) at 60° C.

The BB500 probe hybridized with the HM27 cell line containing the DNA from mouse chromosomes 15 and 17 and revealed the same banding pattern as with total genomic BALB/c DNA. The cell line HM65 that lacks BALB/c chromosome 17 was devoid of hybridizable bands, indicating that the probe did not bind nonspecifically to CHO DNA. DNA from other CHO cell lines containing mouse chromosomes other than chromosome 17 were examined by Southern blotting with the BB500 probe and were found to be negative (not shown). These results indicate that the β-GAP sequences all map to chromosome 17 in the mouse.

Mapping the β-GAP Sequences to the Murine Q/TL Complex

The fact that the β-GAP sequences were isolated from the mouse genome provided several powerful tools to precisely map the location of the sequences. First, the murine MHC is highly characterized, particularly with respect to the nonclassical class I region and, secondly, congenic strains of mice exist where the position of genes in the MHC can be pinpointed. Congenic strains were originally developed by breeding strains of inbred mice together. Subsequent generations of chromosomal crossing over has produced a number of strains which contain a portion of the MHC from one strain and the remainder of the MHC from another strain. Consequently, it is possible to compare restriction fragment length polymorphism (RFLP) between the strains, and determine if the banding patterns are linked to a given MHC locus (for review see Klein, *Natural History of the Major Histocompatibility Complex*, 50–73 (1986)). RFLP analysis was performed by obtaining purified genomic DNA from the various mouse strains, digesting the DNA with EcoRI and performing Southern hybridization with the β-GAP6 BB500 probe as described above. The Southern blot showed that the probe identified up to ten different bands from the DNA of the mouse strains tested (Table 1). Four of these bands, 30 kb, 20 kb, 16 kb and 10.5 kb, were mapped within the MHC locus. The RFLP analysis indicated that there were at least four to six copies of the β-GAP sequences/genome depending on the strain of mouse tested. In addition genetic analysis of the RFLP patterns indicated that the 30 kb and 10.5 kb β-GAP bands mapped to Q region between Q1 and Q4 while the 20 kb and 16 kb β-GAP bands mapped to the T region. In addition, two of the β-GAP sequences that did not demonstrate RFLP polymorphism were mapped telomeric to the classical class I genes.

Locating the β-GAP Sequences Directly Adjacent to Nonclassical Class I Genes

The two of the β-GAP gene sequences that were mapped to the Q region between Q1 and Q4, were directly linked to Q1 and Q2 by DNA sequence analysis of Q1 and Q2 genes isolated from a C57BL/6 (H-2$^b$) λ library. Sequencing showed that both the Q1 and Q2 genes are associated in a head to head configuration with an unknown gene (currently defined as the β-GAP gene) with both genes transcriptionally regulated by a single promoter/enhancer region having two promoters defined by a pair of CAAT and TATA boxes located about 25 bp apart on opposite strands of the DNA. Thus, having intact promoters and a common regulatory region, the class I and β-GAP genes would be transcribed from opposite strands, with the class I genes Q1 or Q2 transcribed from 5' to 3' on the top strand and the β-GAP gene transcribed from 5' to 3' on the bottom strand.

The sequence analysis of Q1 and Q2 genes from C57BL/6, as well as a TL gene from A/J (H-2$^a$, Watts et al. *EMBO J.* 8:1749–1759 (1980)) indicated that β-GAP promoter and regulatory regions had replaced the typical classical class I-type 5' regulatory sequences known to be involved in the regulation of classical class I genes. The β-GAP promoter is an active promoter since it is known that the Q2 gene expresses a gene product that can be detected in the intestine (Wang et al., *Immunogenet.*, 38:370–372 (1993)). These results indicate that the β-GAP promoter regulates the expression of some nonclassical class I genes.

TABLE 1

COMPARISON OF SOUTHERN BLOT ANALYSIS OF EcoRI DIGESTS OF MURINE DNA USING THE BB500 LOW COPY NUMBER PROBE WITH GENETIC MAPS OF VARIOUS ALLOGENEIC AND CONGENIC STRAINS.

| STRAIN | MHC REGION | | | | ECORI BAND SIZE (kb) | | | | | | | | | |
|---|---|---|---|---|---|---|---|---|---|---|---|---|---|---|
| | K | D | Q | T | 30 | 20 | 16 | 14.5 | 13 | 10.5 | 9.2 | 8.0 | 7.8 | 7.5 |
| B6, B10 | b | b | b | b | + | | + | + | | | | | + | + |
| B6, K1 | b | b | k | k | | | + | + | | + | | | + | + |
| B6, K2 | b | b | bk | k | + | | + | + | | | | | + | + |
| AKR | k | k | k | k | | | + | + | | + | | | + | + |
| B6, K3 | k | k | b | a | + | + | + | | | | | | + | |
| B6, K4 | k | k | k | a | | + | + | | | + | | | + | + |
| B6-H-2$^k$ | k | k | k | k | | | + | + | | + | | | + | + |
| B6-Tla$^a$ | b | b | b | a | + | + | + | | | | | | + | + |
| A/J | k | d | a | a | | + | | | | + | + | | + | + |
| Balb/cJ | d | d | d | d | | + | + | + | | + | + | + | | |
| B10, A | k | d | a | a | | + | | + | | + | + | | + | + |
| A-Tla$^b$ | k | d | a | b | | | + | | | + | + | | + | + |

Head to head gene structure with co-regulation of the genes has been previously described in organisms ranging from bacteria to humans, indicating that co-regulation is a widely adopted strategy. (Brickman et al., *J. Molec. Biol.*, 212:669–682 (1990); Xu and Doolittle, *Proc. Natl. Acad. Sci. (USA)*, 87:2097–2101 (1990); Lennard and Fried, *Molec. Cell. Biol.*, 11:1281–1294 (1991); Heikkila et al., *J. Biol. Chem.*, 268:24677–24682 (1993); Fererjian and Kafatos, *Dev. Biol.*, 161:37–47 (1994); Sun and Kitchingman, *Nucleic Acids Res.*, 22:861–868 (1994)). In both prokaryotic and eukaryotic systems, interaction between, or linkage in a metabolic pathway of two gene products has been suggested (Galvalas, et al., *Mol. Cell. Biol.*, 13:4784–4792 (1993); Lightfoot et al., *Br. J Cancer*, 69:264–2673 (1994)). It should be noted that in the β-GAP clones so far studied, the Q1 and Q2 genes still possesses their own CAAT and TATA elements, and it is only the typical classical class I regulatory enhancer regions which are absent.

Conservation of the β-GAP Sequences Across Species

To demonstrate that the β-GAP sequences are conserved, and that various species, including human, contain multiple copies of these genes a "Zoo blot" of various species of genomic DNAs was digested with EcoRI and analyzed by Southern blotting using the murine β-GAP6 BB500 probe. Under low stringency the blot showed detection of a multiplicity of bands in DNA from human, rat, mouse, dog, rabbit and monkey. This indicates that multiple copies of the β-GAP sequences were found in many species including human. In addition, the conservation of the β-GAP multigene family predates speciation of murine and human and therefore is not the product of a recent gene duplication or rearrangement. The demonstration of interspecies sequence homology is significant because, in general, exons and regulatory regions tend to be conserved. Thus, the pattern of specific regions of retained homology suggests that the β-GAP sequences are retained by selective pressure.

Homology Between The β-GAP Sequences and the Promoters for β-globin

Sequences within all six of the 500 bp β-GAP clones show striking sequence and positional homology to mouse, rabbit and human β-globin promoter regulatory elements. Important regulatory elements within a 106 bp region of the β-globin promoter have been characterized (Myers et al., *Science* 232:613–618 (1986); Stuve and Myers, *Mol. Cell Biol.* 6:3350–3358 (1990)). Using saturation mutagenesis and 5' deletion promoters, Myers and his colleagues constructed a series of mutants that were used to identify four regulatory sequences. The four regulatory motifs were located between positions –95 and –26 which contain a CACCC element (positions –95 to –87), CCAAT and TATA box motifs at positions –79 to –72 and –30 to –26, respectively, and a 11 bp repeat element located between the CCAAT and TATA boxes (positions –53 to –32) that contains 2 imperfect duplicated repetitive elements (βDRE). The fact that these βDRE are essential for the expression of globin genes has been shown by deletional studies.

Comparison of the six 500 bp β-GAP sequences with the β-globin promoter sequences from various species showed several striking sequence homologies to β-globin regulatory elements. Analysis of the β-GAP sequence in this region revealed 5 regulatory motifs found in the β-globin promoters. These include the 5' CACCC erythroid element between positions –127 to –123, CCAAT and TATA box motifs between positions –109 to –105 and –30 to –26, respectively, the cap consensus sequence positions –13 to –10, and a fifth and more complex regulatory element involved a β-globin βDRE of a 10 and 11 bp sequence (base pair numbering was determined from sequence alignments with gaps inserted and does not reflect the true base pair position from the transcriptional start site).

In all the β-GAP clones, two of the four βDRE regulatory motifs were flanked by the CCAAT and TATA elements between positions –54 and –32, while two other βDREs were found immediately upstream of the TATA box (positions –11 to +1 and +3 to +12). All of these βDRE were conserved in sequence, and moreover, two of them were conserved in position (–54 and –32). It is significant that the βDREs conserved in β-GAP were conserved in globins from multiple species (mouse, rabbit, chicken and human) covering more than 100 million years of evolution. This observation of evolutionary conservation indicates the β-GAP genes are old genes.

A final putative regulatory motif from the β-GAP clones was AGATAA (nucleotides –82 to –77), which is identical to the DNA consensus sequence for the transcriptional binding factors NF-E1. This family of DNA binding proteins (NF-Ela, b, and c) are involved in the erythroid and/or T-cell specific expression of many genes, including mouse and chicken adult β-globin, the heme pathway enzyme porphobilinogen (PGB) deaminase, the T-cell receptor and the leukemia virus HTLV III.

A closer inspection of the regions of homology between the β-GAP and mouse β-globin promoters reveals several features: 1) 18 of 26 base pairs match at positions –35 to –10 encompassing the consensus TATA motif (Bucher, *J. Mol. Biol.* 212:563–578 (1990)); 2) a region encompassing the β-GAP CCAAT box, positions –113 to –109 contains the β-globin regulatory element CACCC which has been shown to be essential for the appropriate expression of β-globin in erythroid cells; 3) a perfect match of the CCAAT element exists at positions –109 to –105; 4) the fourth matching region encompasses a βDRE element, located between the CCAAT and TATA boxes at positions –64 to –45 (this region contains 16 of 19 bp matches with no gaps); and 5) a consensus cap site sequence as defined by Bucher (Bucher, supra, 1990) and a putative transcriptional start site is identified at nucleotides –13 to +1.

Several other putative regulatory sequences are apparent in the β-GAP promoter. Between positions –68 and –37 and beginning 5 nucleotides distal of the TATA element are 4 palindromes. The 5 base pair repeat TCAGA appears twice within 24 base pairs. These repeats flank and are found within a globin-like imperfect direct repeat element (positions –57 to –47). Two longer palindromes with imperfect dyad symmetry of 12 bp, and 15 bp, positions –67 to –56 and –51 to –37, respectively, contain smaller internal palindromes of 7 bp, CCTCAGG (–66 to –60) and 5 bp repeat, TCAGA (–46 to –42), respectively. This β-GAP 33 bp βDRE-like region combining the two large 12 and 15 bp imperfect palindromes, the β-globin imperfect direct repeat element and the two TCAGA palindromic repeats shows about 50% (16/33) nucleotide sequence homology to the mouse β-globin promoter.

Expression of Genes Immediately Downstream From the β-GAP Sequences in the Gastrointestinal Tract The pattern of specific regions of retained homology between the β-globin regulatory motifs and β-GAP promoters suggests: 1) the sequences have diverged from a common ancestral gene; and 2) the preserved regions in the β-GAP sequences play a critical role in the regulation of expression of their respective genes. Furthermore, the homology to promoters for genes intimately involved in iron metabolism, the occurrence of erythroid specific regulatory sequences, and the close proximity of these genes to the human locus responsible for hemochromatosis, indicates a role for the β-GAP genes in iron metabolism.

To demonstrate that the β-GAP promoters regulate downstream messages, it is imperative to show that the associated genes encode transcribable messages. Moreover, such messages should be expressed in tissues involved in iron absorption, i.e. the gastrointestinal tract, if they are to be involved in the pathogenesis of hemochromatosis.

Northern blotting was performed with poly A+ RNA from various organs including the gastrointestinal tract. The blot was developed using two probes derived from a β-GAP (Q2$^b$) cosmid clone. Total cellular RNA was prepared by the TRIzol™ Reagent method according to the manufacturer's instruction (Gibco/BRL, Gaitherburg, Md.). poly A+ or mRNA was purified by oligo dT cellulose chromatography (Strategene, San Diego, Calif.). RNA was analyzed on formaldehyde-agarose gels and transferred to Zeta Bind membranes as previously described (Evans, et al., *Proc. Natl. Acad. Sci.* (USA) 81:5532–5536 (1984)). The cosmid clone containing a β-GAP sequence that was used for the probe was obtained from a λ library. The clone was digested with ApaLI and KpnI to yield a 10 kb fragment. The fragment was partially digested with BamHI to yield a 2 kb probe encompassing the β-GAP sequences and a 8 kb probe piece further downstream containing the coding sequences for a β-GAP gene.

Northern blotting with the 2 kb probe showed the presence of polydisperse messages produced in tissues from stomach, duodenum, jejunum, spleen and liver, principally of 5 kb and 8 kb in size. The kidney showed less polydispersity with only the 8 kb band predominating. These results indicate that β-GAP promoter and upstream β-GAP coding sequences are expressed in the gastrointestinal tract and are associated with members of a multigene family of which the 5 Kb message of the jejunum is most prominent. The fact that this probe also recognized a band in the liver, spleen, kidney and stomach, suggested that related members of a β-GAP family can be functioning in other tissues. The downstream 8 Kb probe identified a band about 5 kb in jejunum which was absent in from the kidney polyA+ RNA. This result indicates that downstream β-GAP coding sequences are less conserved and can be restricted in expression.

The size and complexity of the β-GAP mRNA products detected by northern blotting is consistent with β-GAP genes coding for a family of large proteins. These characteristics are more like those of a mucin protein family rather than an ion transport family of molecules. The homology to β-globin promoters, the occurrence of erythroid specific regulatory sequences and close proximity of nonclassical class I and β-GAP genes to the locus responsible for hemochromatosis in humans, an inheritable disease of iron metabolism indicates a role for the β-GAP genes and the nonclassical class I genes in iron metabolism. With this information in hand and the facts disclosed herein that β$_2$M-knockout mice have an unusually high incidence of hepatomas led to the understanding that these mice have a metabolic and pathological condition similar to hemochromatosis.

Isolation of Murine β-GAP cDNAs from a Mouse Jejunal Library

The 2 kb β-GAP cosmid probe was used to screen a mouse jejunal cDNA library (Strategene λ ZAP Express kit). Northern blots suggested that the messages recognized by the β-GAP probe were abundant (bands were visible after only three hours of exposure) and this observation was confirmed upon screening the library. Approximately 0.5% of the clones gave a positive signal on the initial screening. 30 positive clones were picked and rescreened, and 26 positive clones were picked from the secondary screen. The murine clones ranged in size from approximately 2 kb to >8 kb, and the size of the inserts corresponded to the bands seen by northern blotting with the 2 kb probe.

DNA purified from the selected murine cDNA clones were digested with EcoRI and subjected to Southern blot analysis. The blot was probed with the 2 kb β-GAP cosmid probe, and 5 were found to be positive indicating they contained β-GAP genes. These β-GAP clones are nearly full length cDNA since they were quite large and since they were isolated with a 5' β-GAP probe.

Cloning of the Human β-Gap Genes

A human genomic DNA library produced in sCOS cosmid vector was prepared as described previously for producing a mouse genomic library in sCOS (Strategene, San Diego Calif.). The isolation of the human β-GAP genes from the human sCOS cosmid library was performed by screening clones with a class I MHC probe. The probe was generated from exons 4 and 5 of the HLA-A2 gene, which encodes the highly conserved β$_2$M binding domain and the transmembrane region. Twenty five putative clones containing class I sequences were detected, and the Cosmids from these clones were purified, cut with the restriction enzyme EcoRI, run on a 0.7% agarose gel and blotted onto a charged nylon membrane. The blot was hybridized with the class I probe, striped and rehybridized with the 2 kb β-GAP probe. Three unique clones were found that reacted with both the murine β-GAP probe and the human class I probe. This result indicates that the human β-GAP genes can be isolated and have a genomic structure with a closely linked class I gene as was observed in mice and rats.

EXAMPLE II

β$_2$M KNOCKOUT MICE DEVELOP IRON OVERLOAD SIMILAR TO HEMOCMROMATOSIS

This example provides a method to analyze iron deficiency in an animal model where an MHC-encoded leczyme function has been genetically deleted. In addition, these mice are useful for evaluating the in vivo utility of carbohydrate ligands on the treatment of hemochromatosis and various iron related diseases such as atherosclerosis, arthritis or cancer.

The data concerning iron overload in the β$_2$M knockout mice is contained in Rothenberg and Voland, 1994. Histologic examination of tissues from 12–18 month old knockout mice, contained on a standard diet, revealed evidence of hepatic necrosis. Iron stains of the tissues revealed iron deposition in the liver of all animals, and in the kidney, or the lung of approximately 10% of the animals. The standard diet contains 350 mg/kg Ferric carbonate. When animals were placed on a "breeder diet", which contains in addition to ferric carbonate, 10 mg/kg ferrous sulfate, iron stores rose dramatically. Iron deposition in the animals was also age related with the highest levels of iron seen in the oldest animals. Together these data indicate that the β$_2$M-knockout mice develop iron overload that is diet and age related. In addition we have shown that the animals develop hepatomas and others have reported that older animals develop diabetes (Faustman et al., *Science* 254: 1756–1761 (1991)). This constellation of pathologies mirrors human hemochromatosis.

Although the invention has been described with reference to the examples provided above, it should be understood that various modifications can be made without departing from the spirit of the invention. Accordingly, the invention is limited only by the claims.

I claim:

1. A method to identify an individual having or predisposed to having hemochromatosis, comprising the steps of:
   a. providing a nonclassical MHC class I heavy chain from the individual; and
   b. detecting an association of said heavy chain with said β2 microglobulin, wherein a reduced association of said heavy chain with said β2 microglobulin compared to the association of a control heavy chain with said β2 microglobulin identifies said individual as having or predisposed to having hemochromatosis.

2. A method to identify an individual having or predisposed to having hemochromatosis, comprising the steps of:
   a) providing from the individual a sample containing a gene encoding a nonclassical MHC class I heavy chain, and
   b) detecting a mutation in said gene, which mutation results in the reduced ability of said heavy chain to associate with said $\beta_2$ microglobulin, wherein the presence of said mutation identifies said individual as having or predisposed to having hemochromatosis.

3. The method of claim 2, wherein said mutation eliminates a signal for the addition of a phosphate group.

4. The method of claim 2, wherein said mutation eliminates the ability of a phosphate group in said heavy chain to be de-phosphorylated in a cell.

5. The method of claim 2, wherein said mutation is determined by nucleic acid sequencing.

6. The method of claim 2, wherein said mutation is determined by polymerase chain reaction.

7. The method of claim 2, wherein said mutation is determined by nucleic acid hybridization.

8. The method of claim 2, wherein said mutation is in a sequence of said gene encoding an α3 domain.

9. The method of claim 2, wherein said sample comprises an epithelial cell.

10. The method of claim 1 or claim 2, wherein said nonclassical MHC class I heavy chain is HLA-X, HLA-E, HLA-J, HLA-H, HLA-G, or HLA-F.

11. The method of claim 1 or claim 2, wherein said nonclassical MHC class I heavy chain is CD1.

* * * * *

UNITED STATES PATENT AND TRADEMARK OFFICE
CERTIFICATE OF CORRECTION

PATENT NO. : 5,674,681

DATED : October 7, 1997

INVENTOR(S) : Rothenberg

It is certified that error appears in the above-identified patent and that said Letters Patent is hereby corrected as shown below:

Column 31, line 8, replace "with said" with --"with a"--.

Column 31, line 21, replace "with said" with --"with a"--.

Signed and Sealed this

Sixteenth Day of November, 1999

Attest:

Attesting Officer

Q. TODD DICKINSON

Acting Commissioner of Patents and Trademarks